US00PP16115P3

(12) United States Plant Patent

McKenry

(10) Patent No.: US PP16,115 P3
(45) Date of Patent: Nov. 15, 2005

(54) GRAPE PLANT NAMED 'RS-9'

(50) Latin Name: ***Vitis champinii*×(*Vitis riparia*×*Vitis rupestris***
Varietal Denomination: RS-9

(75) Inventor: Michael McKenry, Fresno, CA (US)

(73) Assignee: The Regents of the University of California, Oakland, CA (US)

( * ) Notice: Subject to any disclaimer, the term of this patent is extended or adjusted under 35 U.S.C. 154(b) by 66 days.

(21) Appl. No.: 10/656,533

(22) Filed: Sep. 4, 2003

(65) Prior Publication Data

US 2005/0055750 P1 Mar. 10, 2005

(51) Int. Cl.[7] ..... A01H 5/00
(52) U.S. Cl. ..... Plt./205
(58) Field of Search ..... Plt./205

(56) References Cited

PUBLICATIONS

FPMS Grape Program Newsletter [online]. Oct. 2001 [retrieved on Aug. 9, 2004]. Retrieved from the Internet: http://fpms.ucdavis.edu/Grape//GrapeNewsletterOct2001.html>.*

Hashim. Poor Vigor and Chlorotic Leaves in New Princess Plantings May be an Effect of Grapevine Leafroll Virus Nov./Dec. 2001 [online], [retrieved on Aug. 9, 2004]. Retrieved from the Internet.* <http://ucce.ucdavis.edu/counties/cekern/newsletterfiles/From the Vines2700.pdf>.*

Anwar, Safdar A. et al.; "Developmental Response of a Resistance–Breaking Population of *Meloidogyne arenaria* on *Vitis* SPP."; 2002, *Journal of Nematology*, vol. 34, No. 1, pp. 28–33.

Anwar, Safdar A. et al.; "Penetration and Development of *Meloidogyne arenaria* on Two New Grape Rootstocks"; 2002, *Journal of Nematology*, vol. 34, No. 2, pp. 143–145.

Anwar, Safdar A. et al.; "A Search for More Durable Grape Rootstock Resistance to Root–knot Nematode"; 2002, *Am. J. of Enology and Viticulture*, vol. 53, No. 1, pp. 19–23.

Anwar, Safdar A. et al.; "Penetration, Development and Reproduction of *Meloidogyne Arenaria* on Two New Resistant *Vitis* SPP."; 2000, *Nematropica*, vol. 30, No. 1, pp. 9–17.

McKenry, M.V. et al.; "Interactions of Selected Rootstocks with Ectoparasitic Nematodes"; 2001, *Am. J. Enol. Vitic.*, vol. 52, No. 4, pp. 304–309.

McKenry, M.V. et al.; "Interactions of Selected *Vitis* Cultivars with Endoparasitic Nematodes"; 2001, *Am. J. Enol. Vitic.*, vol. 52, No. 4, pp. 310–316.

* cited by examiner

*Primary Examiner*—Anne Marie Grunberg
*Assistant Examiner*—June Hwu
(74) *Attorney, Agent, or Firm*—Townsend and Townsend and Crew, LLP

(57) ABSTRACT

A new and distinct grape (*Vitis vinifera* L. species), RS-9, which is useful as a rootstock, is distinguished by providing broad resistance to nematodes.

3 Drawing Sheets

Latin name of genus and species claimed: 'RS-9' is an interspecific variety of *Vitis champinii*×(*Vitis riparia*×*Vitis rupestris*).

Variety denomination: The name of the variety claimed is 'RS-9'.

BACKGROUND OF THE INVENTION

The invention relates to a new and distinct variety of the *Vitis* L. with broad nematode resistance.

The new variety, 'RS-9', is the result of an interspecific cross of the grape varieties 'Ramsey' (*Vitis champinii*) and 'Schwarzmann' (*Vitis riparia*×*Vitis rupestris*). 'RS-9' plants were asexually reproduced in Parlier, Calif. by the rooting of callused cuttings from dormant, lignified canes in spring or the rooting of green shoots under greenhouse mist in summer.

BRIEF SUMMARY OF THE INVENTION

The present invention provides a novel grape variety having the characteristics described and illustrated herein. 'RS-9' exhibits broad resistance to nematodes and can be used as a rootstock.

DETAILED DESCRIPTION OF THE INVENTION

Figure 1:
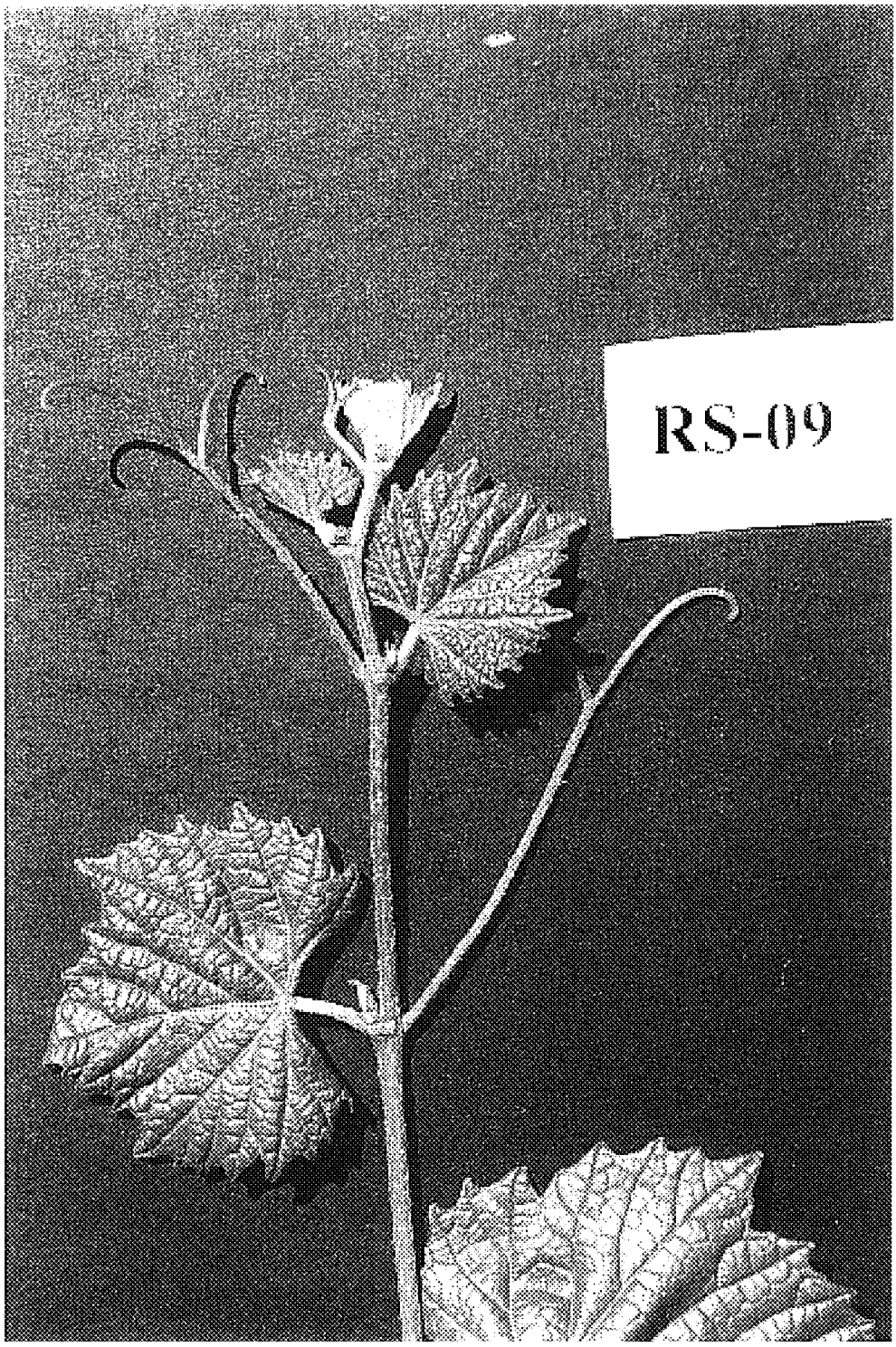
FIG. 1 illustrates a close-up photo of the 'RS-9' shoot tip.
Figure 2:
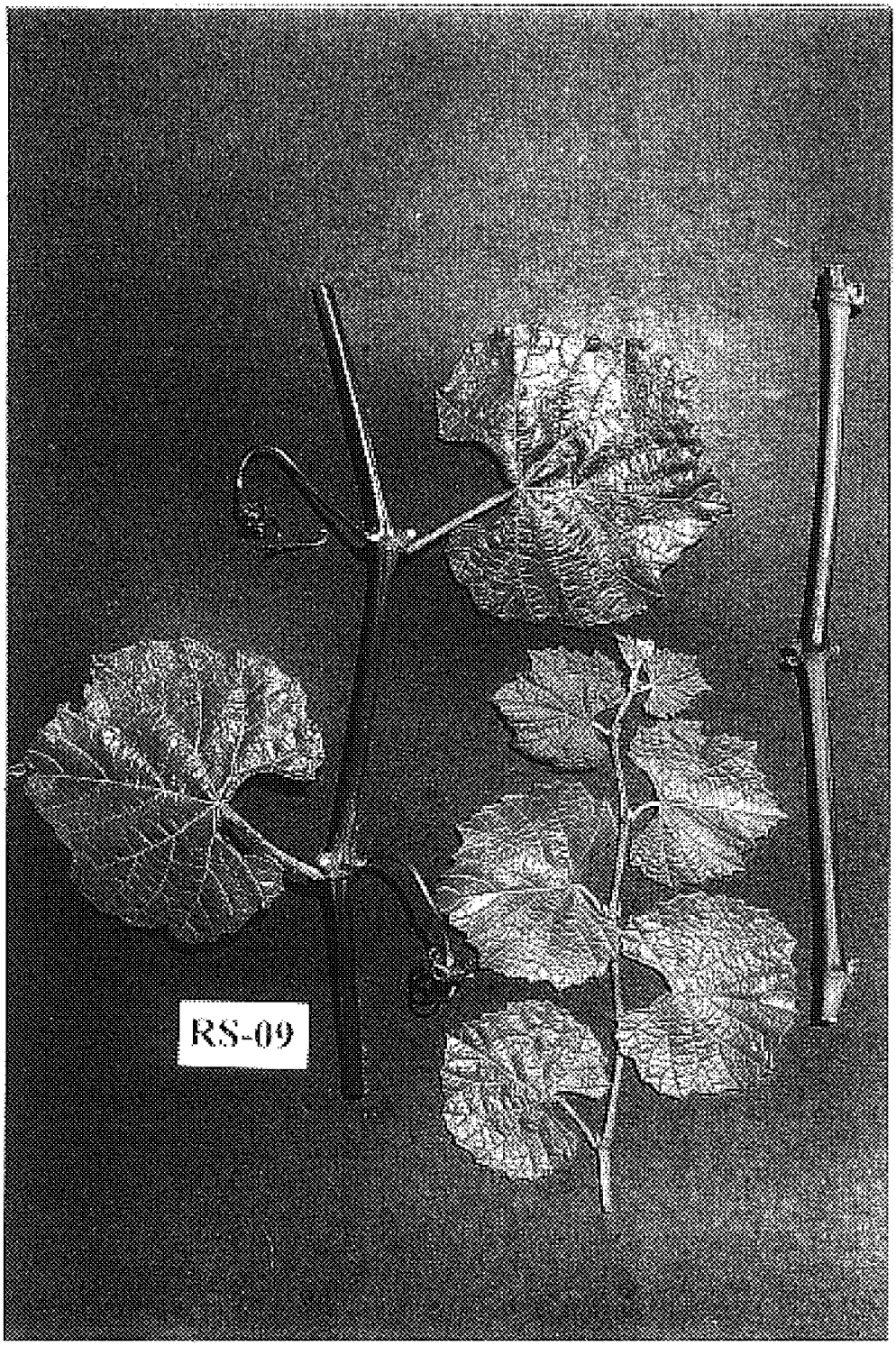
FIG. 2 illustrates a two-node section of primary shoot (upper, exposed side of mid shoot) with leaves attached far left), section of primary shoot (lower, non-exposed side) (far right), and lateral shoot from the same portion of the primary shoot (center of photo).
Figure 3:
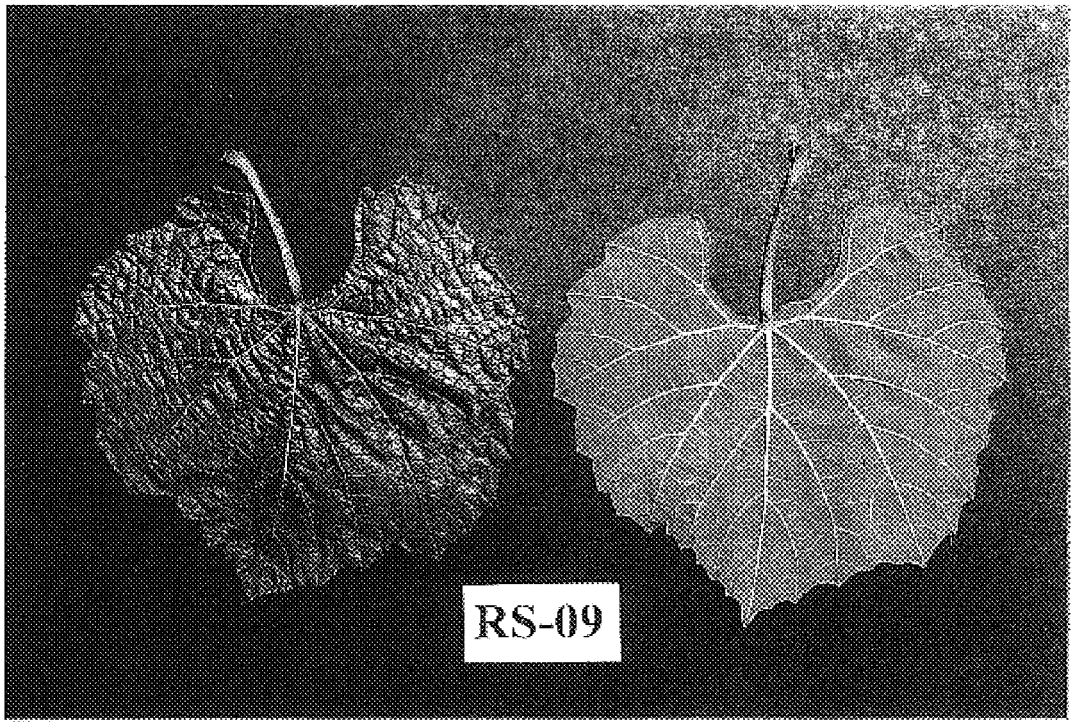
FIG. 3 illustrates an upper (left) and lower (right) sides of leaves from a primary 'RS-9' shoot.
Figure 4:
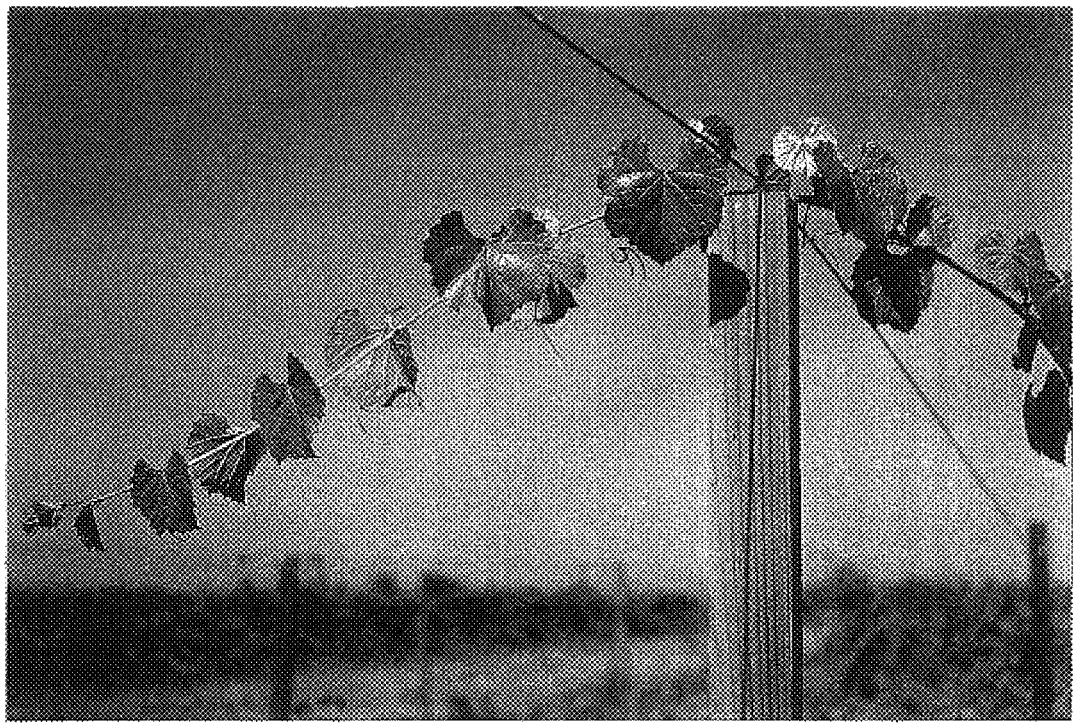
FIG. 4 illustrates a 'RS-9' trailing shoot attached to a trellis wire.

'RS-9' is a rootstock with vigor equivalent to variety Schwarzmann. 'RS-9' is particularly suitable for evaluation in close-planted situations and for coastal valleys and coarse-textured soils.

'RS-9' seedlings readily strike roots and appear generally compatible with scions evaluated thus far.

'RS-9' demonstrates resistance to a gall-initiating *Meloidogyne arenaria* pathotype from grape 'Harmony' and a non-galling *M. chitwoodi* that also attacks 'Harmony'. 'RS-9' exhibits good resistance to *Xiphenema index,* and *Pratylenchus vulnus,* and slight susceptibility to citrus nematode.

'RS-9' offers broader nematode resistance than 'VR 039-16', 'Freedom', 'Harmony', 'Ramsey' or 'Teleki 5C '. Pre- and post-infection resistance mechanisms expressed by *Vitis* rootstocks 'RS-9' and 'Teleki 5C' against-second-stage juveniles (J2) of resistance-breaking populations of *Meloidogyne arenaria* were observed and correlated with juvenile development and nematode reproduction. See, Table 1. Cabernet Sauvignon grape was used as a susceptible control for comparison. Similar numbers of J2 penetrated 'Teleki 5C' and Cabernet Sauvignon roots. Root-tip necrosis, a hypersensitive reaction, occurred in both rootstocks but was effective in reducing J2 penetration only in 'RS-9' roots. Juvenile development occurred in roots of all three rootstocks by 13 days after inoculation, with the highest number of swollen juveniles present in Cabernet Sauvignon roots. Cortical necroses restricted the ability of J2 to reach vascular bundles, thereby restricting access to successful feeding sites and leading to dead or underdeveloped juveniles in 'RS-9' roots. At 35 days after inoculation, only 5% and 25% of the initial inoculum in 'RS-9' and 'Teleki 5C' roots, respectively, reached the adult stage compared to 32% in Cabernet roots. Giant cells were of sufficient size to support nematode development to maturity in Cabernet. Cell necrosis and underdeveloped giant cells were apparent in the resistant rootstocks, which delayed development of adults and limited egg production.

TABLE 1

Penetration and development of a resistance-breaking population of *Meloidogyne arenaria* in roots of three grape rootstocks.

| | Nematodes per root system Days after inoculation | | | | | |
|---|---|---|---|---|---|---|
| Rootstocks | 4 | 13 | 21 | 27 | 35 | Eggs/g root |
| Cabernet (check) | 296 a | 294 a | 272 a | 225 a | 173 a | 403 a |
| Teleki-5c | 282 a | 254 a | 232 a | 183 b | 128 b | 34 c |
| RS-9 | 52 b | 88 b | 49 b | 38 c | 25 c | 81 b |

Data are means of five replications. Means in a column followed by a common letter are not significantly different according to Duncan's multiple range test (P = 0.05).

A botanical description of the 'RS-9' is provided below based on observations and measurements made during the period of Apr. 10 to Aug. 1, 2003 at the University of California Kearney Agricultural Center, 9240 S. Riverbend Avenue, Parlier, Calif. 93648 (Riverbend Avenue, between Manning and Dinuba Avenues, Fresno County). RS-9 rootstock was approximately 10 years old when observed. The vines were irrigated by drip irrigation and row centers were cultivated by disk twice each year. Berms were hand hoes or treated with paraquat contact spray.

Color terminology used in the following description is based on the scheme described in Aloy, John Maerz and M. Rea Paul. A dictionary of color, $2^{nd}$ edition. McGraw-Hill Book Co., New York, 1950. Descriptors for the guidelines for GRAPEVINE (*Vitis.* L), International Union for the Protection of New Varieties of Plants, Geneva, Switzerland are provided.

Vine: Vigorous, semi-drooping in attitude (U.P.O.V.-6.1.5/7). The canopy becomes bushy past midsummer due to numerous, lateral shoots with small leaves. Bud burst early (U.P.O.V.-7.1.2/3)

Shoots:

*Shoot tip.*—Half open (U.P.O.V.-6.1.1/3), downy white.

*Young leaves.*—Light green (U.P.O.V.-6.1.16/1)(Plate 17, I-7) with slight bronzing on tips of serrations; glabrous except for white (U.P.O.V.-6.1.2/1), sparse, prostrate hairs on main veins on lower side (U.P.O.V.-6.1.3/3).

*Internodes.*—Red (Plate 7, C-6) on the exposed, dorsal side (U.P.O.V.-6.1.6/3) and red (Plate 5, I-5) with green stripes on the ventral side (U.P.O.V.-6.1.7/2) in the spring and early summer, becoming light pink (Plate 4, H-3) in midsummer on the dorsal side and light green on the ventral side. Medium prostrate hairs (U.P.O.V.-6.1.11/1). Relief of surface is striate. Length ranges between 5.0–11.5 cm, averaging 8.6 cm. Width ranges between 5–7 mm; mean of 5.8 mm.

*Nodes.*—Coloration is similar to internodes. (U.P.O.V.-6.1.8/3 and U.P.O.V.-6.1.9/2). Width ranges between 6–10 mm; mean of 8.4 mm. Buds average in size, not prominent.

Tendrils: Intermittent, 0-0-2-0-2-0-2 (U.P.O.V.-6.1.14/1). Light green (Plate 1.7, I-7) except for pinkish-red (Plate 5, I-5) pigmentation on basal ⅓. This becomes light pink (Plate 4, H-3) in midsummer growth. Forked. Length is medium, ranging between 9 and 14 cm, averaging 10.85 cm (U.P.O.V.-6.1.15/5). Width ranging between 1–2 mm, averaging 1.5 mm.

Flowers: Male with fully developed stamens and reduced gynoecium (U.P.O.V.-6.2.1/2). Flower clusters small, ranging in length between 3.5 and 6.5 cm and averaging 5 cm. Basal ⅓ of rachis of reddish-pink pigmentation similar to the shoot. Calyptras light green with reddish pigmentation on top and at base (nectaries). Flowers dehisce at onset of bloom.

'RS-9' plants does not produce complete flowers; they only contain male parts. No fruit is produced. The average date of the beginning of bloom is May 5 at Parlier, Fresno County, Calif. The period of bloom lasts 7 to 12 days, depending on the season. The flowers abscise during this period and the flower cluster dries up.

Leaves, blades:

*Shape.*—Reniform (U.P.O.V.-6.1.22/5), entire (U.P.O.V.-6.1.23/1). Open U-shaped petiolar sinus (U.P.O.V.-6.1.30/2) without exposed veins (U.P.O.V.-6.1.32/1).

*Size.*—Small (U.P.O.V.-6.1.21/3). Length ranging between 7.6 and 10.4 cm, averaging 8.8 cm. Width ranging between 8.0 and 10.5 cm, averaging 9.2 cm.

*Appearance.*—Upper surface is dark green (Plate 21, G-7), glabrous and shiny; lower surface is yellowsh-green (Plate 21, E-3), glabrous (U.P.O.V.-6.1 35/1) with short, white upright hairs (U.P.O.V.-6.1.38/3) on the veins. Veins are light green, not prominent; reddish-pink pigmentation near the petiolar sinus, mainly on the basal ⅕ of the inferior lateral veins and becoming faint on midsummer growth (U.P.O.V.-6.1.24/3). Contour is flat (U.P.O.V.-6.1.25/1). Surface is slightly bullate (U.P.O.V.-6.1.26/3).

*Dentation.*—Teeth wide, short (U.P.O.V.-6.1.28/3) and concave (U.P.O.V.-6.1.27/1). P ≦0.25 (height/width of serrations) (U.P.O.V.-6.1.29/1).

Leaves, petioles: Reddish pink (Plate 4, H-3) on dorsal (exposed) side and reddish pink with green stripes on ventral side, becoming light pink on midsummer growth. Medium, prostrate hairs. Length ranges between 3.2 and 4.7 cm, averaging 3.8 cm; width is 2.5 mm (U.P.O.V.-6.1.40/1).

Canes (mature shoots): Lignified, mature shoots in late summer and fall are medium reddish-brown (Plate 7, C-10; U.P.O.V.-6.1.42/4) with striations (U.P.O.V.-6.1.41/3) in the internodes. About every $5^{th}$ or $6^{th}$ striation is of dark brown color, often resulting in 4 or 5 obviously darker striations per internode.

Trunk: The first inner layer of old bark is slightly grayish-brown (Plate 7, A-10). The outer layer is rough, peeling and gray (Plate 7, A-7) due to weathering and trunk expansion.

For purposes of comparison, a similar analysis of parents Schwarzmann and Ramsey performed at the USDA collection at California State University, Fresno. The following is a result of that analysis:

'RAMSEY' ROOTSTOCK

Vine: Vigorous, dense growth; upright in attitude.

Shoots:

*Shoot tip.*—Half open, felty white.

*Young leaves.*—Light, yellowish-green. Medium, prostrate hairs on upper surface. Medium, prostrate hairs on lower surface, especially on the veins and the petiole.

*Internodes.*—Light, yellowish-green. Medium, white tufted hairs or tomentum. Medium in length; small to medium in diameter. Relief of surface is slightly striate.

*Nodes.*—Coloration is similar to internodes. Fewer hairs than on internodes. Buds average in size, not prominent.

Tendrils: Intermittant, 0-0-2-0-2-0-2. Small to medium long and fine; bifurcated. Light, yellowish-green.

Flowers: Female. Small, compact clusters of medium-small black berries.

Leaves, blades:

*Shape.*—Reniform to almost round, slightly 3-lobed. Petiolar sinus deep, open U-shaped.

*Size.*—Medium to medium-small.

*Appearance.*—Upper surface medium dark green with light, prostrate hairs. Lower surface medium green with light green veins and moderate tufted tomentum. Contour is flat. Surface is smooth. Dentation: teeth uniform, straight-sided to slightly concave, shallow and distinct.

Leaves, petioles: Light, yellowish-green with tufted tomentum. Medium in length.

Canes (mature shoots): Lignified, mature shoots in late summer and fall are brown with some darker striations in the internodes. Numerous short to medium lateral shoots are present.

Notable differences between 'RS-9' and 'Ramsey' include: 'RS-9' has horizontal vines whereas 'Ramsey' has vines upright in attitude. The flowers of 'RS-9' are male whereas the flowers of 'Ramsey' are female. The leaf blades of 'RS-9' are large whereas those of 'Ramsey' are medium to medium-small. 'Ramsey' shoots (internodes and nodes) and young leaves are light, yellowish-green; 'RS-9' young leaves have bronzing on the tips of the serrations, and the shoots are reddish on the dorsal side in the spring, becoming light pink in midsummer.

'SCHWARZMANN' ROOTSTOCK

Vine: Vigorous, horizontal in attitude, climbing readily on support wires.

Shoots:

*Shoot tip.*—Closed, shiny green.

*Young leaves.*—Light, yellowish-green. Upper surface glabrous. Sparse, white, prostrate hairs on the petiole and the main veins on the lower surface.

*Internodes.*—Light, yellowish-green with violet-red and green stripes on the upper side. The red coloration becomes more faint in mid to late summer growth. Very sparse, white prostrate hairs. Medium in length and diameter. Relief of surface is slightly striate.

*Nodes.*—Coloration is similar to internodes. Glabrous. Buds average in size, not prominent.

Tendrils: Intermittant, 0-0-2-0-2-0-2. Fairly long and fine, bifurcated. Light, yellowish-green with violet-red coloration, especially on the branches.

Flowers: Male.

Leaves, blades:

*Shape.*—Orbiculo-reniform, entire or slightly 3-lobed. Petiolar sinus wide U-shaped.

*Size.*—Large.

*Appearance.*—Upper surface is glabrous and medium dark green. Lower surface is glabrous and medium light green with short hairs in the veins. Occasional light pink coloration on the main veins at the petiolar junction. Contour is flat. Surface is slightly bullate with more puckering at the petiolar junction. Dentation: teeth irregular, slightly convex, medium large and sharply pointed.

Leaves, petioles: Light, yellowish-green with light red coloration, especially on the upper side. The coloration is more faint in mid and late summer growth.

Canes (mature shoots): Lignified, mature shoots in late summer and fall are medium reddish-brown with striations in the internodes. Strong and long lateral shoots are present under high vigor conditions.

Notable differences between 'RS-9' and 'Schwarzmann' include: 'RS-9' has half open, downy white shoot tips whereas those of 'Schwarzmann' are closed and yellowish-green. 'RS-3' has small leaves whereas 'Schwarzmann' has large leaves. 'Schwarzmann' leaf blades are orbiculo-reniform, sometimes slightly 3-lobed; 'RS-9' leaf blades are reniform in shape and entire.

What is claimed is:

1. A new and distinct variety of grape plant having the characteristics described and illustrated herein.

* * * * *